United States Patent [19]

Gardner et al.

[11] 4,346,991

[45] Aug. 31, 1982

[54] METHOD AND APPARATUS FOR MEASURING RETINAL BLOOD FLOW

[75] Inventors: Keith Gardner; Edward R. Pike, both of Malvern; David W. Hill, London, all of England

[73] Assignee: National Research Development Corporation, London, England

[21] Appl. No.: 199,639

[22] Filed: Oct. 22, 1980

[30] Foreign Application Priority Data

Oct. 31, 1979 [GB] United Kingdom ............... 7937799

[51] Int. Cl.³ .............................................. G01P 3/36
[52] U.S. Cl. .................................. 356/28.5; 128/691; 128/745; 351/16; 356/387
[58] Field of Search ............... 356/28.5, 387; 351/6, 351/7, 8, 16; 128/745, 691

[56] References Cited

U.S. PATENT DOCUMENTS

| | | | |
|---|---|---|---|
| 3,542,472 | 11/1970 | Vaniz | 343/14 |
| 3,753,616 | 8/1973 | Goethert | 356/28.5 |
| 3,966,324 | 6/1976 | Iten | 356/28.5 |
| 4,126,392 | 11/1978 | House | 356/28.5 |
| 4,166,695 | 9/1979 | Hill et al. | 356/28.5 |

OTHER PUBLICATIONS

C. E. Riva, Applied Optics, Jan. 1981, vol. 20, No. 1, p. 117.

*Primary Examiner*—S. C. Buczinski
*Attorney, Agent, or Firm*—Cushman, Darby & Cushman

[57] ABSTRACT

Blood flow in a retinal blood vessel is measured by detecting the doppler shift imparted to two laser beams intersecting on a portion of the retinal vessel. Twin beams of laser radiation are directed along an optical path into an eye and scattered radiation returned along the path into two photo-multipliers. The twin beams are passed through a beam rotator so that the plane containing them can be aligned along the retinal vessel under measurement. A local oscillator signal for homodying with the doppler shifted laser radiation is obtained from reflections from the eye itself or a separate reflector. This reflector can be moved to impart a frequency shift to the local oscillator signal to remove ambiguities in the doppler measurements. Automatic tracking of small eye movements is provided by a beam deflector and servo motor controlled by a detector. Width of the retinal vessel under measurement is obtained by deflecting returning scattered laser radiation and determining the width of the detector signal change.

9 Claims, 7 Drawing Figures

METHOD AND APPARATUS FOR MEASURING RETINAL BLOOD FLOW

This invention relates to a method of and apparatus for measuring retinal blood flow by laser doppler velocimetry.

Laser doppler velocimetry is a technique which allows the measurement of flow velocity by measuring the Doppler shift given to a laser beam scattered from moving particles suspended in the flow. This shift can conveniently be measured by mixing (homodyning) the scattered light with a portion of the original laser beam on the cathode surface of a photodetector. At low light levels the response of the photodetector is a train of discrete output pulses, each corresponding to the absorption of a single photon at the cathode. These pulses are emitted randomly in time if the incident light intensity is constant but when a doppler beat frequency is present, the pulses are rate modulated at this frequency.

The extraction of the doppler frequency from such a train of pulses can be effected by digital photon correlation (see Pike, 1972 Journal of Physics D 5 L23). The photon correlation functions is the Fourier transform of the spectrum of frequencies in the incident light intensity.

Retinal blood flow has previously been measured using laser doppler velocimetry by placing a large contact lens on a patient's eye, directing a beam of laser radiation through the contact lens and measuring light scattered along a second path at an angle to the laser beam. Such a technique is described in Science, Nov. 29, 1974, Vol. 186, pages 830 to 831, and Investigative Opthalmology, Vol. 11, pages 936–944, November 1972. Proc Technical Programme Electro Optics Systems Design Conf. September 1976, article by Riva et al. One drawback with this technique as applied to man is the necessity for the patient to use a comparatively large and uncomfortable contact lens. Another is that such a bistatic system is intrinsically difficult to maintain in alignment in the presence of small eye movements.

In U.K. Patent Ser. No. 1,564,315, U.S. Pat. No. 4,166,695, a single beam of laser radiation is directed along an optical path into a patient's eye, without use of a contact lens and onto a retinal blood vessel. Radiation scattered off blood corpuscles is received back along the optical path and onto a detector. Advantages of this monostatic system are (a) Use of contact lens is not required,
(b) Inherent alignment of the transmitted and reflected beams.

A disadvantage is the difficulty in determining the doppler angle i.e. the angle between the blood vessel and optical path. Additionally any blood flow which lies tangentially to a circle centred on the pole of the eye cannot be measured.

Laser doppler velocimetry enables variation in blood flow velocity with time to be measured with sufficient speed that variations within a heart beat cycle can be observed. Thus it is desirable to illuminate a blood vessel continuously for some time. Unfortunately involuntary eye movements make this extremely difficult. The laser illumination must be small enough to cover just one vessel otherwise blood flowing in adjacent vessels etc. degrades the results. It would be desirable to track the involuntary eye movements to maintain illumination of the desired vessel.

According to this invention a method of measuring retinal blood flow includes the steps of directing two beams of laser radiation along an optical path, directing the two beams into a patient's eye onto a retinal blood vessel, aligning the two beams of radiation in the eye so that the plane containing them also contains the direction of blood flow to be measured, receiving two beams of radiation scattered by blood corpuscles back along the same optical path and processing this scattered radiation to determine a doppler signal and hence blood flow velocity.

Apparatus for carrying out the method of this invention includes a laser for producing a beam of laser radiation, a beam splitter for providing two beams of laser radiation, a polarising prism for transmitting one plane of polarisation and reflecting another plane of polarisation, means for rotating the plane containing the two beams of laser radiation, focussing means for causing intersection of the two laser beams in a patient's eye, deflecting means for directing the two laser beams into the desired part of the eye, means for general illumination of the eye fundus, means for observing the fundus generally and the laser illuminated portions, and detector means for detecting the two beams of laser radiation scattered from within the eye, the arrangement being such that the two laser beams may be directed along the optical path into the eye and laser radiation scattered from a blood vessel is collected as two beams back along the optical path into the detector means.

Preferably the two laser beams are orthogonally polarised to avoid cross talk.

Preferably two detectors are used and doppler signals on both scattered beams detected simultaneously. However, a single detector may be used and the doppler signals in the reflected beams detected sequentially.

A beam deflector may be moved by a servo motor under the control of a signal from a detector to maintain illumination of a desired blood vessel despite small involuntary eye movements. The detector controlling the servo motor may be a third detector whose filtered input receives light less the laser frequency to improve contrast between a blood vessel and its surrounds. Alternatively one of the detectors used for detecting one of the laser beams may have the laser frequency filtered out whilst Doppler measurements are made using the other detector only. In this latter arrangement a glass block may be caused to oscillate in the non signal beam providing an error position signal for use in controlling the servo motor.

The invention will now be described, by way of example only, with reference to the accompanying drawings of which:

Figure 1:
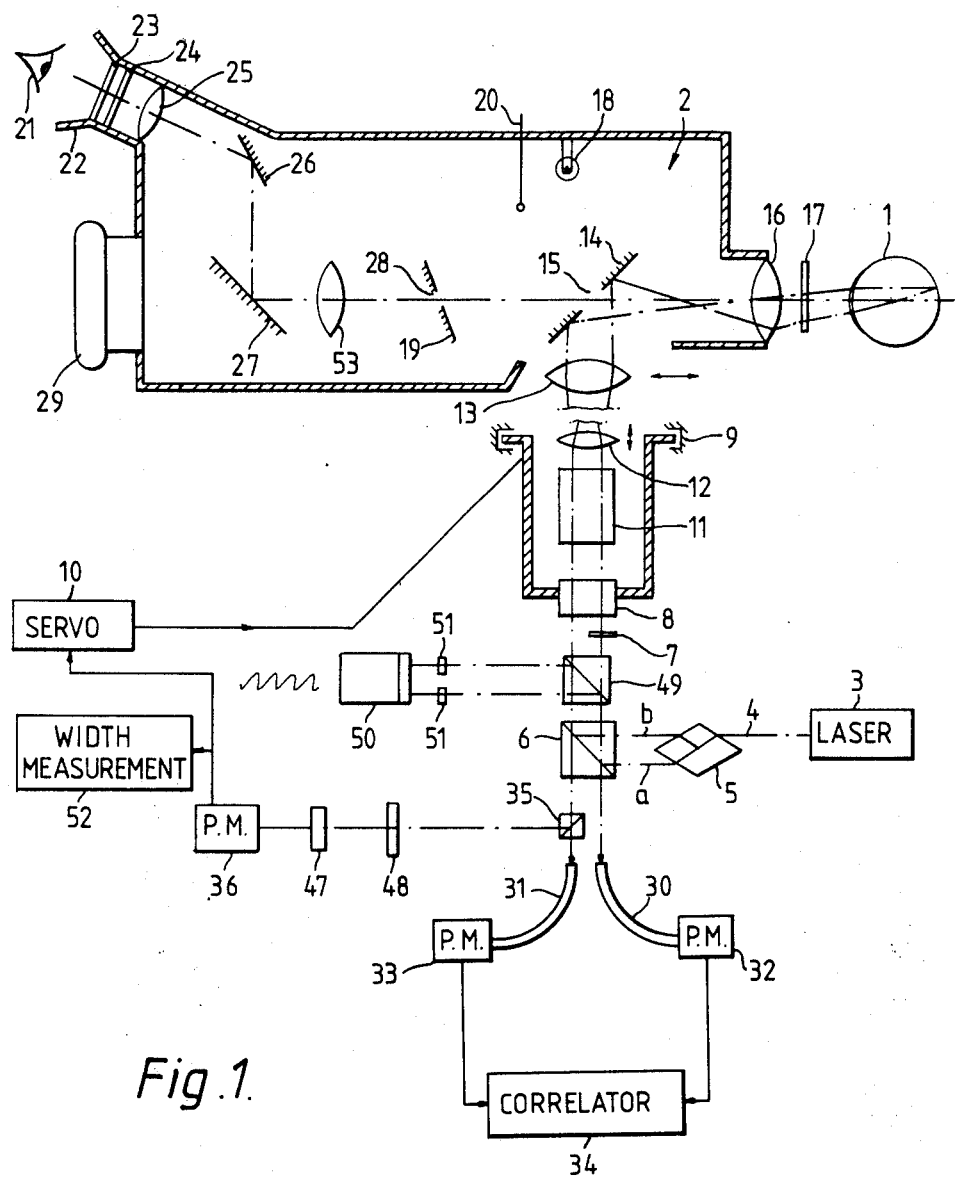
FIG. 1 is a schematic view of a laser doppler velocimeter apparatus.
Figures 3A, 3B:
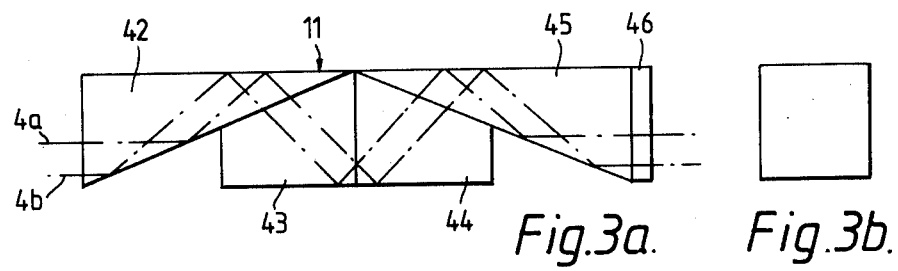
Figure 4:
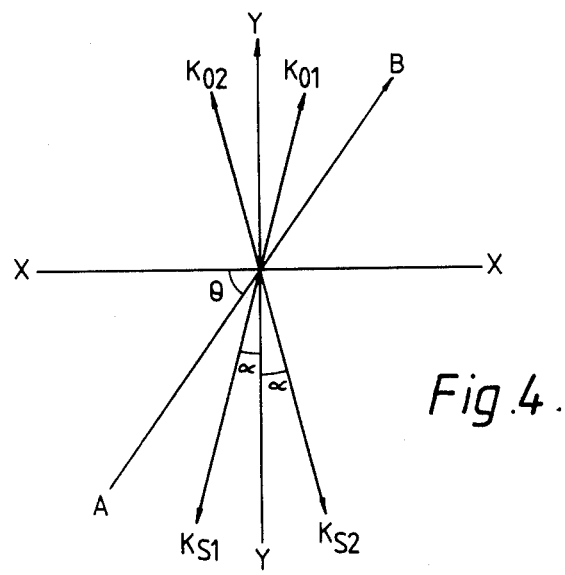
Figure 5:
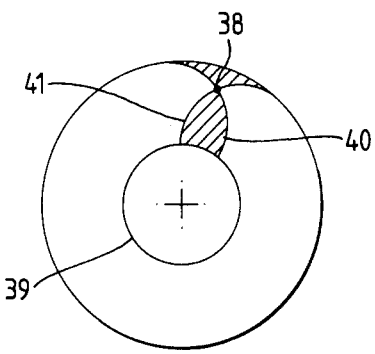
Figure 7:
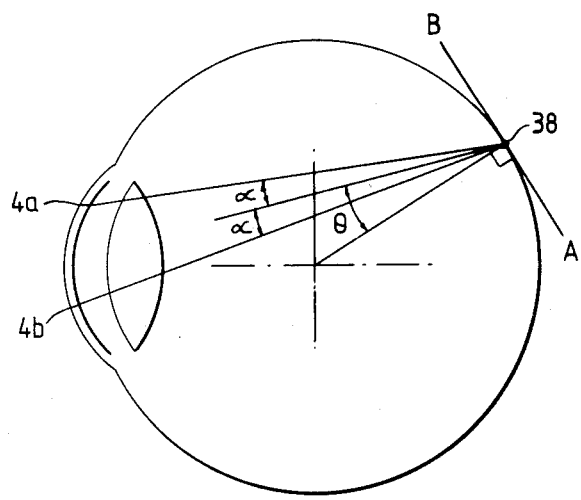
Figure 6:
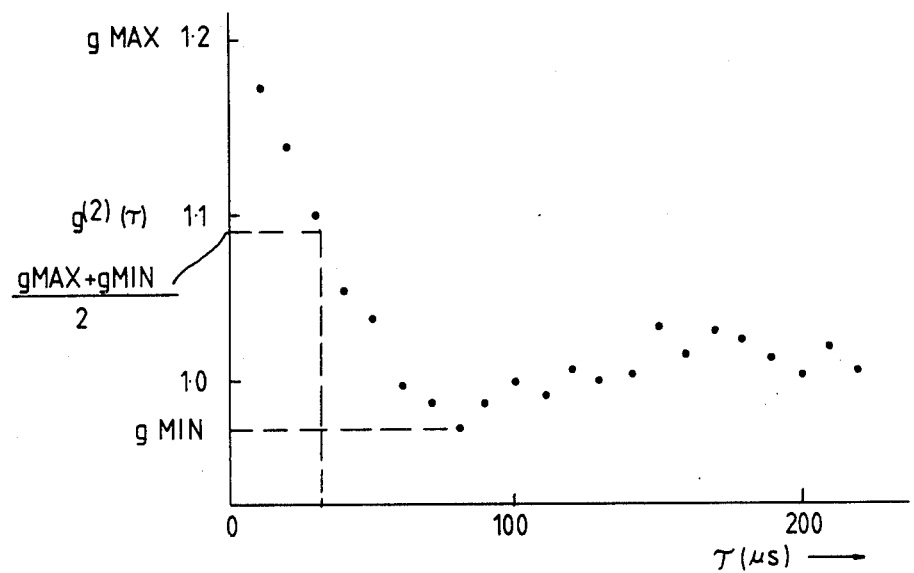

FIGS. 3a, b are side and end views of a prism shown in outline in FIG. 1;

FIG. 4 is a diagram for use in explaining the theory of laser doppler velocimetry;

FIG. 5 is a view of graticules used by an operator in measuring the blood flow;

FIG. 6 shows a typical correlation function obtained during blood flow measurements;

FIG. 7 is a cross-section (non-central) of an eye containing the laser beams and showing their angles.

As shown in FIG. 1 a patient's eye 1 is positioned in front of a fundus camera 2. Light from a 1 milliwatt HeNe laser 3 is attenuated to give about 10 microwatts into the eye 1. The laser beam 4 is split into two beams a, b by a beam splitter 5 and reflected by a polarising beam splitter 6.

A half wave plate 7 is placed in the path of beam a to change its polarisation to horizontal polarisation to reduce cross talk between beams a and b (vertically polarised). A glass prism 8, shown in broken lines, may be used to follow involuntary eye movements in one direction only. To do this the prism is mounted for rotation about an axis 9 normal to and in the plane containing the beams a and b. A servo motor 10 rotates the block upon demand as described later. A beam rotator 11 is rotatable about its length to rotate the plane containing the two beams a, b whilst preserving their polarisation so that the beams both lie along the direction of flow in a retinal vessel. A focussing lens 12 is adjustable to cross the two beams in an image plane at the back of the eye 1. An adjusting lens 13 is movable in a plane normal to the optical axis of the beams to position the beams a, b on any desired part of the retina. A mirror 14 having a central aperture 15 reflects the beams a, b through an aspheric lens 16 and a quarter wave plate 17 (optional) into the eye 1. The quarter wave plate 17 changes the polarisation of beams a, b to left and right circular polarisation. This is not essential as the scattered light is depolarised.

Within the fundus camera 2 a light source 18 provides general fundus illumination. Its light is reflected off a mirror 19 through the aperture 15 and into the eye 1. An adjustable fixation target 20 enables the patient to direct the eye 1 where required.

Observation of the eye 1 by an operator 21 is via an eye piece 22, graticules 23, 24, lenses 25, mirror 26, beam splitter 27 through apertures 28, 15 in the mirrors 19, 14 respectively.

Permanent record of the fundus is by means of a photographic camera 29 attached to the back of the fundus camera 2.

Details of the camera 2 are only diagrammatic since any suitable fundus camera may be used and modified to accept the laser beams.

Returning laser light is collected from the polarising beam splitter 6 by the two fibre optic pipes 30, 31 and delivered to two photo-multipliers 32, 33 acting as light detectors whose outputs are taken to a double channel photon correlator 34 (e.g. Malvern Correlator, manufactured by Malvern Instruments Ltd, Malvern, Worcs.) where the returned laser beams are correlated independently to obtain the doppler signals and hence blood flow velocity.

A local oscillator laser signal for homodyning with a doppler shifted signal on the photomultipliers 32, 33 is provided by reflections from the patients eye. Alternatively part of the laser 3 light is reflected by a partial reflector 49 through aperture stops 51 onto a reflecting surface 50, such as a mirror or a light scattering surface. This reflector 50 is mounted to oscillate rapidly normal to its surface, e.g. by mounting on a piezo electric crystal. A ramp voltage with rapid flyback is applied to the crystal. This provides a frequency shifted local oscillator signal whose frequency shift is greater than any expected doppler shift. Alernatively an electro optic or acousto-optic device may be used to provide the same effect.

A selective reflector 35 in the path of beam b reflects light from the illuminated spot at the frequencies of the light source 18, through a red blocking filter 48 and second glass block 47 to a third photo multiplier 36. Output from the photo multiplier 36 controls the servo motor 10. The filter 48 improves contrast on the photo multiplier by showing blood vessels as two closely spaced dark lines on a lighter background. The glass block 47 is caused to oscillate at a speed much higher then eye movements and provide an error signal that is used by the servo motor in maintaining illumination of the required blood vessel. Additionally movement of the block 47 enables the width of the blood vessel to be measured.

As the block oscillates the signal received by the photo multiplier 36 will change from a high value to a low value as a vessel wall is crossed with the beam, a slightly higher value in the vessel centre, again to a low value across the second wall of the vessel, and then back to a high value clear of the blood vessel. The width of the low value signal is a measure of the blood vessel diameter, and is determined by the width measurement circuit 52. Such a measurement is useful, in conjunction with blood velocity, to indicate blood flow rate.

Figure 2:
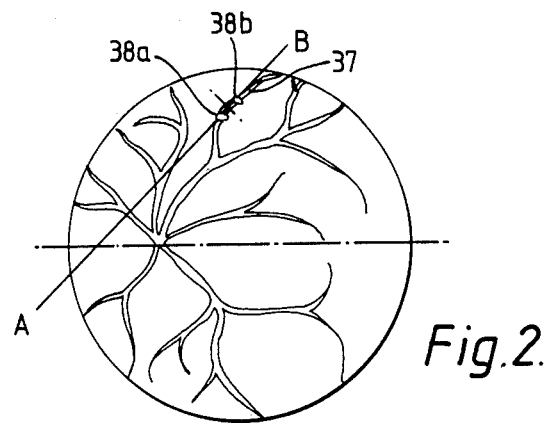
FIG. 2 is a view of the fundux of an eye showing retinal blood vessels.

In operation a mydriatic and cycloplegic drop is instilled into the patients eye to reduce or prevent accommodation. The patient is then positioned in front of the fundus camera 2; the illumination and focus are adjusted in the usual manner to bring the fundus of the eye 1 into view. Direction of gaze is controlled by the patient observing the target 20 or by any other suitable means. An operator 21 is then able to view the fundus FIG. 2 and select a suitable blood vessel 37. The twin beams a, b of laser light are directed onto the selected blood vessel 37 and the beams separated, by movement of lens 12, so that two spots 38a, 38b are observed on the blood vessel 37. The beam rotator 11 is rotated until the two separate spots 38a, 38b both lie along the blood vessel 37. The spots 38a, 38b may then be focussed into coincidence.

Measurement may then begin. Laser radiation scattered from blood corpuscles in the blood vessel 37 pass back through the quarter wave plates 17 and have polarisation planes orthogonal to those from the laser 3. These reflected beams 4a, b pass back along the optical path through the polarising beam splitter 6 (which is transparent to horizontally polarised light) to the photomultipliers 32, 33 and the correlator 34 where the blood velocity is determined.

Involuntary eye movements may cause the blood vessel 37 to move out of the laser illumination 38 if such movement is normal to the blood flow at the point of measurement; movement along the flow will alter the doppler signal but will not cause loss of illumination. To maintain laser illumination despite such eye movement the beams a, b may be servoed to follow the eye movement normal to the blood flow by deflecting both beams with the glass prism 8. When the blood vessel 37 moves out of illumination the signal received by the third photomultipliers 36 changes. This signal change is used to actuate the servo motor 10 and deflect the beams a, b to follow the eye movements. This enables blood flow measurements to be taken continuously over periods of several heart beat cycles.

The theory behind measurement of floow flow velocity by the two beams method is as follows: Blood flow is to be measured along the line AB FIGS. 2, 7. FIG. 4 shows the geometry for calculating the velocity from the measured signals where:

$k_{01}$, $k_{02}$ are input laser wave vectors $k_{S1}, k_{S2}$ are scattered laser wave vectors
$\lambda$ is laser beam wavelength.

The two beams a, b are arranged so that line AB lies in the plane containing the beams.

Consider first the case where only one velocity v is present (not true in practice). The Doppler shift $\Delta\omega$ for the first beam a is given by $$\Delta\omega_1 = (k_{S1} - k_{O1}) \cdot v \qquad (1)$$

$$= \frac{2\pi v}{\lambda} [\cos(90 - \alpha - \theta) - \cos(90 + \alpha + \theta)]$$

$$= \frac{2\pi v}{\lambda} [\sin(\alpha + \theta) + \sin(\alpha + \theta)]$$

$$= \frac{4\pi v}{\lambda} [\sin\alpha \cos\theta + \cos\alpha \sin\theta]$$

for the second beam b $$\Delta\omega_2 = (k_{S2} - k_{O2}) \cdot v \qquad (2)$$

$$= \frac{2\pi v}{\lambda} [\cos(90° - \theta + \alpha) - \cos(90 + \theta - \alpha)]$$

$$= \frac{2\pi v}{\lambda} [\sin(\theta - \alpha) + \sin(\theta - \alpha)]$$

$$= \frac{4\pi v}{\lambda} [\sin\theta \cos\alpha - \cos\theta \sin\alpha]$$

The doppler frequency $\Delta\omega$ can be determined by the known homodyne techniques eg. as described in U.K. Patent Ser. No. 1,564,315. It should be noted however that only $|\Delta\omega|$ is actually measured when using eye reflections for the local oscillator signal.

Subtracting (2) from (1) gives $$\Delta\omega_1 - \Delta\omega_2 = \frac{8\pi v}{\lambda} \sin\alpha \cos\theta \qquad (3)$$

On adding (1) and (2)

$$\Delta\omega_1 + \Delta\omega_2 = \frac{8\pi v}{\lambda} \sin\theta \cos\alpha \qquad (4)$$

from (3) $v \cos\theta = \frac{\lambda}{8\pi \sin\alpha} (\Delta\omega_1 - \Delta\omega_2) \qquad (5)$ From (4) $v \sin\theta = \frac{\lambda}{8\pi \cos\alpha} (\Delta\omega_1 + \Delta\omega_2) \qquad (6)$ $$\therefore v = \left[ \left( \frac{\lambda}{8\pi \cos\alpha} \right)^2 \cdot (\Delta\omega_1 + \Delta\omega_2)^2 + \frac{\lambda}{8\pi \sin\alpha}^2 (\Delta\omega_1 - \Delta\omega_2)^2 \right]^{\frac{1}{2}}$$

$$= \frac{\lambda}{4\pi \sin 2\alpha} [\sin^2\alpha (\Delta\omega_1^2 + 2\Delta\omega_1 \Delta\omega_2 + \Delta\omega_2^2) + \cos^2\alpha (\Delta\omega_1^2 - 2\Delta\omega_1 \Delta\omega_2 + \Delta\omega_2^2)]^{\frac{1}{2}}$$

$$\therefore v = \frac{\lambda}{4\pi \sin 2\alpha} [\Delta\omega_1^2 + \Delta\omega_2^2 - 2\Delta\omega_1 \Delta\omega_2 \cos 2\alpha]^{\frac{1}{2}} \qquad (7)$$

Measurement of v thus requires a knowledge of angle only, which is obtained by calculation of the optics for an average (model) eye, and the two doppler shifts $\Delta\omega_1$, $\Delta\omega_2$.

Since only $|\Delta\omega|$ is measured equation (7) is only correct if $\theta > \alpha$. If $\theta < \alpha$ then $\Delta\omega_2$ should be negative and the negative sign in (7) then becomes positive. Whether the positive or negative sign should be used can determined by reference to an average eye.

Alternatively the graticule 23, 24 of the operators eye piece may be marked by a circle 39, FIG. 5, centred on the pole of the eye 1, the circle 39 marking the boundary between $\theta < \alpha$ (inside the circle) and $\theta > \alpha$. Outside the circle 39 two separately rotatable curves 40, 41 may be moved about the circle's axis to intersect at a measurement spot 38. If a blood flow lies along a line within the shaded areas then $\theta > \alpha$ otherwise $\theta < \alpha$.

As an alternative to using reflections from within the eye 1 as a local oscillator signal, reflection from the reflector 50 may be used. In this case the reflections are conveniently given a frequency shift by moving the reflector 50 as previously noted. Such a frequency shift can be made larger than any doppler shift imparted by blood movement. As a result the sign of $\Delta\omega$ is always known so that equation (3) may be used to determine v.

The angle $\theta$ in practice is small and therefore $\cos\theta$ remains almost at unity. Alternatively $\theta$ can be measured.

Blood flow within a vessel 37 varies from near zero at the walls to a maximum at the centre of the vessel 37. The received doppler signal is thus a sum of frequencies which for a vessel narrow compared with the beam diameter, and assuming a parabolic flow profile results in a correlation function $g(\tau)$ of the form:

$$g(\tau) = \frac{\sin\Delta\omega_m \tau}{\Delta\omega_m \tau} \qquad (8)$$

where $\Delta\omega_m$ is the maximum doppler shift present.

FIG. 6 shows an example of a correlation function obtained from one beam. The value of $\Delta\omega_m$ for each correlation function can be determined either by finding the half height point of the first limb of $g(\tau)$, or by finding the area under the $g(\tau)$ curve; the latter method being less sensitive to noisy data points. Departures from non-parabolic flow may be accounted for by numerical corrections.

FIGS. 3a, b shows details of the beam rotator which may be formed of four prisms 42, 43, 44, 45 cemented together. The beam rotator 11 in FIG. 1 rotates two laser beams about an axis between them whilst retaining their original polarisation state. To do this the refractive index and angles of reflection must be chosen as follows:

Let p=component of light vibrating parallel to a surface
s=component of light vibrating perpendicular to a surface
$n_1$=refractive index of glass
$n_2$=refractive index of air
n is $n_2/n_1$
$\delta$ is phase difference introduced between s and p components
$\theta_i$ is angle between light beam and normal to an interface.

For total internal reflection within a glass block at a glass/air surface $$\theta_i > \theta_{crit}$$

$\theta_{crit}$ is given by $\sin\theta_{crit} = n_2/n_1$ phase difference $\delta$ is given by $$\tan\frac{\delta}{2} = \frac{\cos\theta_i \sqrt{\sin^2\theta_i - n^2}}{\sin^2\theta_i}$$

For the beam rotator 11 there are five reflections controlled by angle $\beta$ for beams entering and leaving normal to the end faces. In the example of FIGS. 3a, b $\beta = 22.7°$, the glass is Schott glass reference BK7, $1/n = 1.515$ at 6328 Å, $\delta = 179.62°$. The prisms act collectively as a half wave plate. A half wave plate 46, with correctly aligned axes, is added to the end of the prisms 42, 43, 44, 45 to provide a zero phase change between the s and p polarisations.

As an alternative form of apparatus for measuring blood flow uses one of the laser detectors 33 (photomultipliers) to provide a signal to the servo motor 10. An initial short time measurement of blood flow is made at a particular spot 38 using the two beams a and b as described above. This enables $\Delta\omega_1$, $\Delta\omega_2$, and v to be determined. From equation, (1) or (2) the other terms are easily determined. Providing the angles $\theta$, $\alpha$ remain constant blood flow measurements of the same spot 38 can continue using only one reflected laser beam 4a. The other laser beam 4b is not required and so its photomultiplier is filtered to remove red laser light (to aid contrast between blood vessels and background) and its output used to control the servo motor 10.

To avoid cross talk between beam a and b without the use of half wave plate 7 and quarter wave plate 17 the spots 38a and 38b may be left slightly apart whilst taking doppler measurements. Cross talk may arise because of the coincidence of spots and depolarisation of the beams on the retina.

I claim:

1. Apparatus for measuring retinal blood flow comprising a fundus camera for observation of the fundus of an eye, a laser for illuminating a portion of a retinal blood vessel, means for detecting laser radiation scattered by the eyes to determine retinal blood flow from the doppler shift imparted to the laser radiation by moving blood corpuscles, and an optical system for directing twin beams of laser radiation along an optical path into the eye and directing radiation reflected by the eye back along the optical path into the detecting means, the optical system including a beam rotator for rotating the plane containing the two beams to align along a retinal blood vessel, and means for causing the twin beams to intersect where required in the eye.

2. Apparatus according to claim 1 wherein the twin beams of laser radiation are orthogonally polarised.

3. Apparatus according to claim 2 wherein the beam rotator preserves the sense of polarisation of the beams passing through it.

4. Apparatus according to claim 3 comprising a reflecting surface for producing a laser radiation local oscillator signal.

5. Apparatus according to claim 4 comprising means for producing a frequency shifted local oscillator signal.

6. Apparatus according to claim 3 comprising a beam deflector and servo motor for maintaining laser illumination of a required retinal blood vessel.

7. Apparatus according to claim 6 comprising a red blocking filter and photomultiplier for applying a correction signal to the servo motor.

8. Apparatus according to claim 6 comprising a beam deflector movable at a high speed to produce an error signal.

9. Apparatus according to claim 3 comprising means for measuring the width of an illuminated retinal blood vessel.

* * * * *